US011667908B2

(12) United States Patent
Oommen et al.

(10) Patent No.: US 11,667,908 B2
(45) Date of Patent: Jun. 6, 2023

(54) PORTABLE NUCLEIC ACID EXTRACTION APPARATUS AND METHOD OF USING THE SAME

(71) Applicant: STEM ARTS PROJECTS, LLC, Lincoln, NE (US)

(72) Inventors: Abraham Oommen, Lincoln, NE (US); Andrew Rush, Lincoln, NE (US); Heather Piscatelli, Lincoln, NE (US); Seth Lewin, Lincoln, NE (US); Brandon Hatch, Lincoln, NE (US)

( * ) Notice: Subject to any disclaimer, the term of this patent is extended or adjusted under 35 U.S.C. 154(b) by 0 days.

(21) Appl. No.: 15/566,600

(22) PCT Filed: Aug. 10, 2016

(86) PCT No.: PCT/US2016/046243
§ 371 (c)(1),
(2) Date: Oct. 13, 2017

(87) PCT Pub. No.: WO2017/027538
PCT Pub. Date: Feb. 16, 2017

(65) Prior Publication Data
US 2018/0105809 A1   Apr. 19, 2018

Related U.S. Application Data

(60) Provisional application No. 62/203,707, filed on Aug. 11, 2015.

(51) Int. Cl.
*C12N 15/10* (2006.01)
*B01L 3/00* (2006.01)
*C12M 1/00* (2006.01)
*B01L 1/00* (2006.01)
*C12Q 1/6806* (2018.01)

(52) U.S. Cl.
CPC ............ *C12N 15/1006* (2013.01); *B01L 1/52* (2019.08); *B01L 3/5029* (2013.01); *C12M 1/00* (2013.01); *C12Q 1/6806* (2013.01)

(58) Field of Classification Search
None
See application file for complete search history.

(56) References Cited

U.S. PATENT DOCUMENTS

| 4,197,361 | A  | * | 4/1980  | Hoff ................... G01N 33/5764 435/5 |
| 6,225,068 | B1 | * | 5/2001  | Wolfrum ............ C12Q 1/6874 422/68.1 |
| 7,018,538 | B2 |   | 3/2006  | Leiser et al. |
| 8,114,027 | B2 | * | 2/2012  | Triva ................. A61F 13/38 600/573 |
| 8,317,728 | B2 | * | 11/2012 | Triva ................. C12M 33/02 600/573 |
| 9,011,358 | B2 | * | 4/2015  | Triva ................. A61F 13/38 604/1 |
| 9,173,779 | B2 | * | 11/2015 | Triva ................. A61B 10/0045 |
| 2003/0124029 | A1 |   | 7/2003  | Webb et al. |
| 2003/0129296 | A1 |   | 7/2003  | Kelso |
| 2003/0215845 | A1 |   | 11/2003 | Bille |
| 2011/0107855 | A1 | * | 5/2011  | Motadel ............ B01L 3/0275 73/863.21 |
| 2011/0203688 | A1 | * | 8/2011  | Reed ................. B01L 3/5027 137/565.11 |
| 2011/0257386 | A1 | * | 10/2011 | Chua ................. C12N 15/1006 536/25.4 |
| 2012/0171712 | A1 | * | 7/2012  | Triva ................. B01L 3/5029 435/29 |
| 2013/0157315 | A1 | * | 6/2013  | Debenham ............ G01N 1/02 435/91.2 |
| 2014/0127796 | A1 | * | 5/2014  | Malik ................. C12M 21/18 435/289.1 |
| 2016/0348092 | A1 |   | 12/2016 | Stray et al. |

FOREIGN PATENT DOCUMENTS

| WO | 1993/015226 A1   | 8/1993  |                |
| WO | WO-9315226 A1  * | 8/1993  | .......... C12Q 1/6813 |
| WO | 2001/044812 A1   | 6/2001  |                |

(Continued)

OTHER PUBLICATIONS

Melzak, K.A., Sherwood, C.S., Turner, R.F. and Haynes, C.A., 1996. Driving forces for DNA adsorption to silica in perchlorate solutions. Journal of colloid and interface science, 181(2), pp. 635-644. (Year: 1996).*

Adamowicz, M.S., Stasulli, D.M., Sobestanovich, E.M. and Bille, T.W., 2014. Evaluation of methods to improve the extraction and recovery of DNA from cotton swabs for forensic analysis. PloS one, 9(12), e116351 pp. 1-18. (Year: 2014).*

Belloy, E., Thurre, S., Walckiers, E., Sayah, A. and Gijs, M.A.M., 2000. The introduction of powder blasting for sensor and microsystem applications. Sensors and Actuators A: Physical, 84(3), pp. 330-337. (Year: 2000).*

(Continued)

*Primary Examiner* — Teresa E Strzelecka
*Assistant Examiner* — Olayinka A Oyeyemi
(74) *Attorney, Agent, or Firm* — Baird Holm LLP (57) ABSTRACT

A portable nucleic acid extraction kit includes a portable nucleic acid extraction apparatus, at least one lysis buffer, at least one binding buffer, at least one washing buffer, at least one elution buffer, and at least three kit sample tubes. The portable nucleic acid extraction apparatus includes a handle, a rod, a tip, and may include a nucleic acid binding medium. The method of using the portable nucleic acid extraction apparatus includes, treating a biological sample having a nucleic acid, binding the nucleic acid in the treated biological sample to the tip of the portable nucleic acid extraction apparatus, incubating the tip of the portable nucleic acid extraction apparatus bound with the nucleic acid, washing the tip of the portable nucleic acid apparatus bound with the nucleic acid, eluting the bound nucleic acid, and analyzing the eluted nucleic acid.

11 Claims, 4 Drawing Sheets

(56) References Cited

FOREIGN PATENT DOCUMENTS

| WO | 2005105309 A1 | 11/2005 | |
| WO | WO-2005105309 A1 * | 11/2005 | ............ B01L 3/0255 |
| WO | 2014/116813 A1 | 7/2014 | |
| WO | WO-2014116813 A1 * | 7/2014 | ............... C07H 1/06 |

OTHER PUBLICATIONS

Fouckhardt et al., 2007. nm-and μm-scale surface roughness on glass with specific optical scattering characteristics on demand. Advances in OptoElectronics, vol. 2007, Article ID 27316, pp. 1-7. (Year: 2007).*

Wensink et al., Jan. 23-27, 2000. High resolution powder blast micromachining. In Proceedings IEEE 13th Annual International Conference on Micro Electro Mechanical Systems (MEMS 2000), Miyazaki, Japan, Jan. 23-27, 2000; (Cat. No. 00CH36308), pp. 769-774. (Year: 2000).*

Wang, X., Cooper, K.L., Wang, A., Xu, J., Wang, Z., Zhang, Y. and Tu, Z., 2006. Label-free DNA sequence detection using oligonucleotide functionalized optical fiber. Applied physics letters, 89(16), pp. 163901-1 to 163901-3. (Year: 2006).*

ISR/WO dated Dec. 15, 2016 for related application PCT/US16/46243, 14 pages.

Anandika Dhaliwal, DNA Extraction and Purification, https://www.labome.com/method/DNA-Extraction-and-Purification.html, accessed on Oct. 13, 2017.

Ex parte James Stray, Jason Yingjie Liu, Maxim Brevnov, Jaiprakash Shewale, and Allison Holt, decision of the Patent Trial and Appeal Board, Appeal No. 2014-001388, U.S. Appl. No. 12/882,194, 7 pages.

Direct adsorption of ssDNA to polystyrene for characterization of the DNA/anti-DNA interaction, and immunoassay for anti-DNA autoantibody in New Zealand White mice., Lacy, MJ, Voss, EW. Journal of Immunological Methods, 116 (1989) 87-98.

Interchim: "Nucleic acids preparation/DNA&RNA Purification", Jul. 10, 2014 (Jul. 10, 2014), pp. 1,9.

Weibel, Curtis, "The Spotting Accelerator", Customizable Head Assembly For Advanced Microarraying, Point Technologies, Inc., Aug. 1, 2014, pp. 1-6.

Protocols & Applications Guide, Promega, Aug. 31, 2012, pp. 1-35.

Sigma Aldrich: "Deoxyribonucleic Acid (DNA) Spooling Educational Kit", Jul. 19, 2005 (Jul. 19, 2005), XP055623739. Retrieved from the Internet: URL: https://www.sigmaaldrich.com/ content/dam/sigma-aldrich/docs/Sigma/Bulletin/d8666bul.pdf [retrieved on Sep. 18, 2019].

Scilabware: "laboratory glassware, plasticware & accessories (extracts of the 2015 catalogue)", Apr. 1, 2015 (Apr. 1, 2015), XP055623747. Retrieved from the Internet: URL: https://www.scilabware.com/pub/media/wysiwyg/literature/ SciLabware_2015_Main_Catalogue_Low_Res_English_1_.pdf [retrieved on Sep. 18, 2019].

Analytik Jena [online], innuSPEED Tissue DNA Kit, 2011, [retrieved May 1, 2020], www.analytik-jena.co.jp/fileadmin/content/pdf_life_science/Manual/Manual_innuSPEED_Tissue_DNA_Kit.pdf.

Sapporo College of Science and Technology [online], "Hands-On Genetic Engineering Study, Welcome to the Fascinating World of DNA" [non-official translation], Oct. 20, 2014 [retrieved May 1, 2020], s-kagisen.ac/jp/201410201129.

Sho-Oh College of Life Science and Technology [online], "Bio Trial Entry & Learning about Work 5." [non-official translation] Bio News [non-official translation], No. 1042, Aug. 30, 2018, [retrieved May 1, 2020], sho-oh.ac.jp/blog/bio/2012/08/no10425.html.

Decision to Grant for related application JP 2018-506348 dated Apr. 20, 2021, 3 pages.

English translation of Granted Claims for related application JP 2018-506348 issued Apr. 20, 2021, 8 pages.

Examination Report for related application AU 2016306451 dated Mar. 19, 2021, 5 pages.

Examination Report for related application NZ 740585 dated Mar. 12, 2021, 4 pages.

Stolzle-Oberglas Gmbh: "COPAN-ESwab(TM)", Jun. 17, 2015 (Jun. 17, 2015), XP055710300, Wien, Austria. Retrieved from the Internet: URL: http://www.labshop.stoelzle.com/shop_hacc/1545651721/dokumente/ESWAB_Abstrichtupfer_COPAN.pdf, 2 pages (p. 2 is an unofficial translation of p. 1).

Patent Examination Report 1 for related application NZ 740585 dated Jul. 30, 2020, 6 pages.

Notice for Reasons for Rejection Office Action for related application JP 2018-506348 dated Jun. 2, 2020, 42 pages (references previously cited in IDS filed Aug. 4, 2020 and noted in the Notice begin on p. 14).

Partial Supplementary European Search Report, including the Provisional Opinion, dated Nov. 29, 2018 for EP Patent Application No. 16835800.0, 18 pages.

Supplementary European Search Report dated Mar. 1, 2019, including the Extended European Search Report dated Feb. 12, 2019, for EP Patent Application No. 16835800.0, 17 pages.

EPO Communication dated Jul. 6, 2020 for EP Patent Application No. 16835800.0, 7 pages.

Stolzle-Oberglas Gmbh: "COPAN-ESwab(TM)", Jun. 17, 2015 (Jun. 17, 2015), XP055710300, Wien, Austria. Retrieved from the Internet: URL: http://www.labshop.stoelzle.com/shop_hacc/1545651721/dokumente/ESWAB_Abstrichtupfer_COPAN.pdf.

EPO Communication pursuant to Article 94(3) EPC and attached examination, dated Jun. 7, 2020 and dated Sep. 24, 2019 for EP Patent Application 16835800.0, 7 pages.

Office Action from GPTO, dated Mar. 6, 2017, 8 pages. Relevance: D1 US 2014/0127796 (previously cited in an IDS and D2 WO 2014/116813 (previously cited in an IDS) to consider independent claims 1, 11, and 16 to lack inventinve step over D1 in combination with D2.

Verdon TJ, et al., 'Swabs as DNA collection devices for sampling different biological materials from different substrates', J Forensic Sci. Jul. 2014;59(4):1080-1089. doi: 10.1111/1556-1029.12427. Epub Feb. 6, 2014. PMID: 24502761, 10 pages.

Examination Report for related application AU 2016306451 dated Feb. 4, 2022, 4 pages.

Notice of acceptance for patent application AU 2016306451 dated Mar. 16, 2022, 3 pages.

Decision to Grant from GPTO, dated Jan. 31, 2018, 8 pages. Relevance: GTPO decision to grant based on response to prior rejection dated Mar. 6, 2017 (cited on IDS filed Jan. 7, 2022).

Notice of Acceptance of patent No. 740585, dated Jun. 1, 2021, 2 pages.

* cited by examiner

PORTABLE NUCLEIC ACID EXTRACTION APPARATUS AND METHOD OF USING THE SAME

REFERENCE TO RELATED APPLICATIONS

This application is national stage entry under 35 U.S.C. § 371(f) of PCT/US16/46243 entitled "Portable Nucleic Acid Extraction Apparatus and Method of using the Same" filed Aug. 10, 2016, which claims the benefit of priority to U.S. Provisional Patent Application No. 62/203,707, filed Aug. 11, 2015, entitled "Nucleic Acid Extraction Apparatus and Method of Use Thereof", which are both incorporated by reference in their entirety.

BACKGROUND

Methods for nucleic acid (e.g. deoxyribonucleic acid (DNA) and ribonucleic acid (RNA)) extraction generally include four common elements: cell lysis for release of nucleic acids, binding of the nucleic acid to a nucleic acid binding medium, washing of the bound nucleic acid to remove cellular components other than the nucleic acids from the bound nucleic acid, and elution (release) of the bound nucleic acid from the nucleic acid binding medium. Conventional nucleic acid extraction from a biological sample is carried out by a variety of different extraction techniques, including, organic extraction, magnetic separation, silica-based extraction, and anion exchange. These methods typically utilize diverse equipment including centrifuges, pipettes, columns and/or other equipment that requires technical expertise to use effectively. Further, such conventional methods typically require anywhere from 12 to 24 steps to complete, which are labor intensive, reducing efficiency.

Typically, the nucleic acid binding medium remains stationary and takes the form of a solid medium, such as a silica-based and anion-exchange column. The biological sample is applied to the nucleic acid binding medium via pipettes or other automated systems. Next, buffers are applied to the medium either manually or through an automated system to first bind and then elute nucleic acids. These methods generally employ centrifuges to separate the nucleic acid components from the remaining cellular components. The use of pipettes, centrifuges, and other automated equipment requires technical expertise to operate, and may increases the time required to extract nucleic acids. Methods of nucleic acid extraction that utilize such equipment are not conducive to utilization in a field scenario (e.g. on a farm, ranch, or at the point of care in an underserved area) and/or by an individual with little to no technical training.

Another nucleic acid extraction method utilizes magnetic separation to eliminate the need of centrifuges to separate bound nucleic acid from the other cellular components. However, the magnetic beads used in such methods are typically added in free form to the sample, thus requiring the use of a magnet or other automated machine to maneuver and contain the beads by a skilled operator. Further, this method is time intensive, again inhibiting its widespread use in a field scenario by an individual without technical expertise.

As molecular diagnostics are gaining popularity, there have been world-wide efforts to eliminate or reduce the limitations of existing nucleic acid extraction techniques, particularly in field scenarios, as on-site extraction may reduce barriers to subsequent analysis. It is therefore desirable to eliminate the need for technical expertise, the use of specialized equipment, and the stationary nucleic acid binding medium used in nucleic acid extraction to make nucleic acid extraction available in a field scenario or laboratory setting. Further it is desirable to reduce the number of steps necessary to extract nucleic acids to increase efficiency of methods to nucleic extract nucleic acids.

SUMMARY

In a first aspect, the present invention relates to a portable nucleic acid extraction apparatus for nucleic acid extraction, comprising a handle, a rod attached to the handle, a tip attached to the rod, wherein the tip is configured to bind nucleic acids.

In another aspect, the present invention relates to a method for extracting nucleic acid from a biological sample comprising nucleic acid containing cells, the method comprising the following steps (a) through (f): (a) adding lysis buffer to the biological sample; (b) adding binding buffer to the mixture obtained in step (a); (c) dipping the tip of a portable nucleic acid extraction apparatus according to the present invention into the mixture obtained in step (b); (d) incubating the tip of the portable nucleic acid extraction apparatus in the mixture obtained in step (b); (e) washing the tip of the portable nucleic acid extraction apparatus with a washing buffer; and (f) eluting nucleic acid bound to the tip of the portable nucleic acid extraction apparatus with an elution buffer.

In a third aspect, the present invention relates to a portable nucleic acid extraction kit comprising a portable nucleic acid extraction apparatus according to the present invention; at least one lysis buffer; at least one binding buffer, at least one washing buffer, at least one elution buffer, and at least three kit sample tubes.

BRIEF DESCRIPTION OF THE DRAWINGS

The numerous advantages of the present invention may be better understood by reference to the accompanying figures in which:

FIG. 1.*a*. depicts a portable nucleic acid extraction apparatus.

FIG. 1.*b*. depicts a portable nucleic acid extraction apparatus comprising nucleic acid binding fibers.

FIG. 1.*c*. depicts a portable nucleic acid extraction apparatus comprising nucleic acid binding beads.

FIG. 1.*d*. depicts a portable nucleic acid extraction apparatus comprising nucleic acid binding proteins.

FIG. 1.*e*. depicts a portable nucleic acid extraction apparatus made of glass and having an increased surface area.

FIG. 3.*a*. summarizes the concentration [ng/µl] and purity [A260/280] of six genomic DNA samples obtained with the portable nucleic acid extraction.

FIG. 3.*b*. illustrates the results of PCR amplifications using genomic DNA samples obtained with the portable nucleic acid extraction apparatus as DNA template.

FIG. 3.*c*. illustrates the results of RCA using genomic DNA samples extracted with the portable nucleic acid extraction apparatus as a template.

DETAILED DESCRIPTION

In a first aspect, the present invention relates to a portable nucleic acid extraction apparatus. The portable nucleic acid extraction apparatus comprises a handle, a rod, and a tip. Typically, the rod is attached to the handle and the tip is attached to the rod. The tip is configured to bind nucleic acids.

Within the context of the present invention, the term "binding nucleic acids" means that free nucleic acids which are present in solution can be directly bound to the tip of the portable nucleic acid extraction apparatus. "Free" nucleic acids means that the nucleic acids are not present within a cell but have been released from a cell. Within the context of the present invention, the term "binding nucleic acids" refers to molecular binding and includes covalent and non-covalent binding of nucleic acids to the tip of the portable nucleic acid extraction apparatus. Non-covalent interactions that may contribute to the binding of nucleic acids to materials such as silica, silica-derived materials, polystyrene and glass but also to biomolecules such as certain proteins include electrostatic interactions such as ionic interactions and hydrogen bonding and Van der Waals forces. Within the context of the present invention, the term "mixture" means a solution, a suspension, or a mixture.

Within the context of the present invention, the term "configured to bind nucleic acids" means that the tip is either made of material which is able to bind nucleic acids that are present in solution or comprises structures that are able to bind nucleic acids that are present in solution. These structures may be made of nucleic acid binding material (nucleic acid binding medium) such as glass, polystyrene, silica or silica-derived materials, and may additionally be shaped such that the nucleic acid binding surface of the tip is increased. For instance, the tip of the portable nucleic acid extraction apparatus may comprise fibers, such as polystyrene fibers and silica fibers, or beads such as polystyrene beads, silica beads and glass beads. The tip of the portable nucleic acid extraction apparatus may also comprise at least one nucleic acid binding protein, such as streptavidin.

In particular embodiments, the portable nucleic acid extraction apparatus includes a nucleic acid binding medium attached to the tip, where nucleic acid binding medium is configured to bind nucleic acids.

In particular embodiments, the tip is made of a material which is able to bind nucleic acids and/or the tip comprises at least one structure which is configured to bind nucleic acids.

In particular embodiments, wherein the tip is made of a material selected from at least one of the group consisting of wood, plastic, polystyrene, functionalized polystyrene, glass, and a silica-derived material.

In particular embodiments, the handle, the rod, and the tip are formed as a single piece. In particular such embodiments, the handle, the rod, and the tip are made of a material selected from at least one of the group consisting of wood, plastic, polystyrene, functionalized polystyrene, glass, and a silica-derived material. Particularly, the handle, the rod and the tip are made of glass.

In particular embodiments, the tip and optionally the handle and/or the rod are made of glass, and the tip and optionally the handle and/or the rod are sandblasted. Sandblasting increases the surface area of the tip and optionally the handle and/or the rod, and thereby increases the surface that may be bound by nucleic acids.

In particular embodiments, the material which is able to bind nucleic acids is selected from at least one of the group consisting of polystyrene, functionalized polystyrene, glass, and silica-derived material.

In particular embodiments, the at least one structure which is configured to bind nucleic acids is selected from the group consisting of at least one fiber, at least one bead, at least one protein and any combination thereof.

In particular embodiments, the at least one fiber is selected from a silica fiber, a polystyrene fiber and a combination thereof.

In particular embodiments, the at least one bead is selected from the group consisting of a silica micro bead, a silica nano particle, a polystyrene micro bead, a polystyrene nano particle, a sand-blasted glass bead, and any combination thereof.

In use, the tip of the portable nucleic acid extraction apparatus is inserted into a first sample tube containing a biological sample comprising free nucleic acids, i.e. nucleic acids that are not present within a cell. Typically, a biological sample comprising nucleic acid containing cells is first treated with lysis buffer to allow for cell lysis and nucleic acid release into the sample solution to form a mixture. After lysis buffer addition, the tip of the portable nucleic acid extraction apparatus is inserted into the mixture. The tip is then incubated in the mixture to allow for binding of the nucleic acids to the tip. After incubation, the tip with nucleic acids bound to its surface is removed from the first sample tube and inserted into a second sample tube containing washing buffer to wash the nucleic acids bound to the tip. The tip with washed nucleic acids bound to its surface is then inserted into a third sample tube containing elution buffer for elution, i.e. to allow for release of the bound nucleic acids from the tip into the elution buffer. The eluted nucleic acids may be further analyzed.

Thus, in a second aspect, the present invention relates to a method for extracting nucleic acid from a biological sample comprising nucleic acid containing cells, the method comprising the following steps: (a) adding lysis buffer to the biological sample; (b) adding binding buffer to the mixture obtained in step (a); (c) dipping the tip of a portable nucleic acid extraction apparatus according to the present invention into the mixture obtained in step (b); (d) incubating the tip of the portable nucleic acid extraction apparatus in the mixture obtained in step (b); (e) washing the tip of the portable nucleic acid extraction apparatus with washing buffer; and (f) eluting nucleic acid bound to the tip of the portable nucleic acid extraction apparatus with an elution buffer.

In particular embodiments, the method further comprises the step of adding ethanol to the biological sample before or during step (a) and/or to the mixture obtained in step (a) before or during step (b) and/or to the mixture obtained in step (b) before or during step (c) or before or during step (d).

In particular embodiments, the lysis buffer is an aqueous buffer comprising tris-hydrochloride; the binding buffer is an aqueous buffer comprising sodium hypochlorite and glycine-hydrochloride and having a pH of from about 2.0 to 4.0, preferably of about 3.0; the washing buffer is an aqueous buffer comprising glycine-hydrochloride and ethanol; and the elution buffer is an aqueous buffer comprising tris-hydrochloride and having a pH of from about 7.0 to about 10.0, preferably of about 8.8.

In particular such embodiments, the lysis buffer is an aqueous solution of tris-hydrochloride, optionally further comprising at least one substance selected from the group consisting of lysozyme, proteinase K, sodium hydroxide and any combination thereof; the binding buffer is a mixture of aqueous sodium hypochlorite and aqueous glycine-hydrochloride having a pH of from about 2.0 to 4.0, preferably of about 3.0; the washing buffer is a mixture of aqueous glycine-hydrochloride and aqueous ethanol; and the elution buffer is aqueous tris-hydrochloride having a pH of from about 7.0 to about 10.0, preferably of about 8.8.

In particular embodiments, the lysis buffer is selected from the group consisting of an aqueous buffer comprising from 0.2 to 5 percent, preferably about 1 percent (v/v) triton x-100, an aqueous buffer comprising from 2 to 50 millimolar, preferably about 10 millimolar tris-hydrochloride, an aqueous buffer comprising ethylenediaminetetra-acetic acid and having a pH of from about 5.5 to about 7.5, preferably of about 6.5, and any combination thereof; the binding buffer is selected from the group consisting of an aqueous buffer comprising sodium hypochlorite and glycine-hydrochloride and having a pH of from about 2.0 to about 4.0, preferably of about 3.0, an aqueous buffer comprising tris-hydrochloride and sodium acetate/acetic acid and having a pH of from 3.6 to 5.6, an aqueous buffer comprising sodium citrate/citric acid and having a pH of from 3.0 to 6.2, an aqueous buffer comprising sodium perchlorate, an aqueous buffer comprising sodium nitrate, an aqueous buffer comprising from 4 to 5 molar sodium chloride, an aqueous buffer comprising from 4 to 5 molar potassium chloride, an aqueous buffer comprising from 4 to 6 molar guanidine-hydrochloride, an aqueous buffer comprising from 4 to 6 molar guanidine thiocyanate, an aqueous buffer comprising from 4 to 6 molar iodide, an aqueous buffer comprising from 4 to 6 molar urea, and any combination thereof; the washing buffer is selected from the group consisting of an aqueous buffer comprising from 5 to 7, preferably 6 molar sodium perchlorate, an aqueous buffer comprising from 5 to 7, preferably 6 molar sodium nitrate, an aqueous buffer comprising from 4 to 5 molar sodium chloride, an aqueous buffer comprising 4 to 5 molar potassium chloride, an aqueous buffer comprising 4 to 6 molar guanidine-hydrochloride, an aqueous buffer comprising 4 to 6 molar guanidine thiocyanate, an aqueous buffer comprising from 4 to 6 molar iodide, an aqueous buffer comprising from 4 to 6 molar urea, an aqueous buffer comprising from 100 to 300 millomolar, preferably about 200 millimolar glycine-hydrochloride, and any combination thereof; and/or the elution buffer is selected from the group consisting of ultrapure water, an aqueous buffer comprising tris-hydrochloride and having a pH from 7.4 to 9, an aqueous buffer comprising from 0.05 to 0.2 millimolar, preferably about 0.1 millimolar ethylenediaminetetra-acetic acid, and any combination thereof In particular such embodiments, the lysis buffer is selected from the group consisting of 0.2 to 5 percent, preferably about 1 percent (v/v) triton x-100 in water, aqueous 2 to 50 millimolar, preferably about 10 millimolar tris-hydrochloride, aqueous ethylenediaminetetra-acetic acid having a pH of from about 5.5 to about 7.5, preferably of about 6.5, in each case optionally further comprising at least one substance selected from the group consisting of lysozyme, proteinase K, sodium hydroxide and any combination thereof; the binding buffer is selected from the group consisting of a mixture of aqueous sodium hypochlorite and aqueous glycine-hydrochloride having a pH of from about 2.0 to about 4.0, preferably of about 3.0, a mixture of aqueous tris-hydrochloride and aqueous sodium acetate/acetic acid having a pH of from 3.6 to 5.6, aqueous sodium citrate/citric acid and having a pH of from 3.0 to 6.2, aqueous sodium perchlorate, aqueous sodium nitrate, aqueous 4 to 5 molar sodium chloride, aqueous 4 to 5 molar potassium chloride, aqueous 4 to 6 molar guanidine-hydrochloride, aqueous 4 to 6 molar guanidine thiocyanate, aqueous 4 to 6 molar iodide, aqueous 4 to 6 molar urea, and any combination thereof; the washing buffer is selected from the group consisting of aqueous 5 to 7, preferably 6 molar sodium perchlorate, aqueous 5 to 7, preferably 6 molar sodium nitrate, aqueous 4 to 5 molar sodium chloride, aqueous 4 to 5 molar potassium chloride, aqueous 4 to 6 molar guanidine-hydrochloride, aqueous 4 to 6 molar guanidine thiocyanate, aqueous 4 to 6 molar iodide, aqueous 4 to 6 molar urea, aqueous 100 to 300 millomolar, preferably about 200 millimolar glycine-hydrochloride, and any combination thereof and/or the elution buffer is selected from the group consisting of ultrapure water, aqueous tris-hydrochloride having a pH from 7.4 to 9, aqueous 0.05 to 0.2 millimolar, preferably about 0.1 millimolar ethylenediaminetetra-acetic acid, and any combination thereof.

In particular embodiments, the lysis buffer comprises at least one substance selected from the group consisting of lysozyme, proteinase K, sodium hydroxide and any combination thereof In a third aspect, the present invention relates to a portable nucleic acid extraction kit comprising: a portable nucleic acid extraction apparatus according to the present invention; at least one lysis buffer; at least one binding buffer; at least one washing buffer; at least one elution buffer; and at least three sample tubes.

In particular embodiments, the kit further comprises ethanol.

Preferably, the kit includes at least 50 portable nucleic acid extraction apparatuses, at least 150 kit sample tubes, and a first bottle containing a volume of lysis buffer to lyse at least 50 samples, a second bottle containing a volume of binding buffer to bind nucleic acids of at least 50 samples, a third bottle containing a volume of washing buffer to wash at least 50 samples, and a fourth bottle containing a volume of elution buffer to elute nucleic acids of at least 50 samples.

Figure 1:
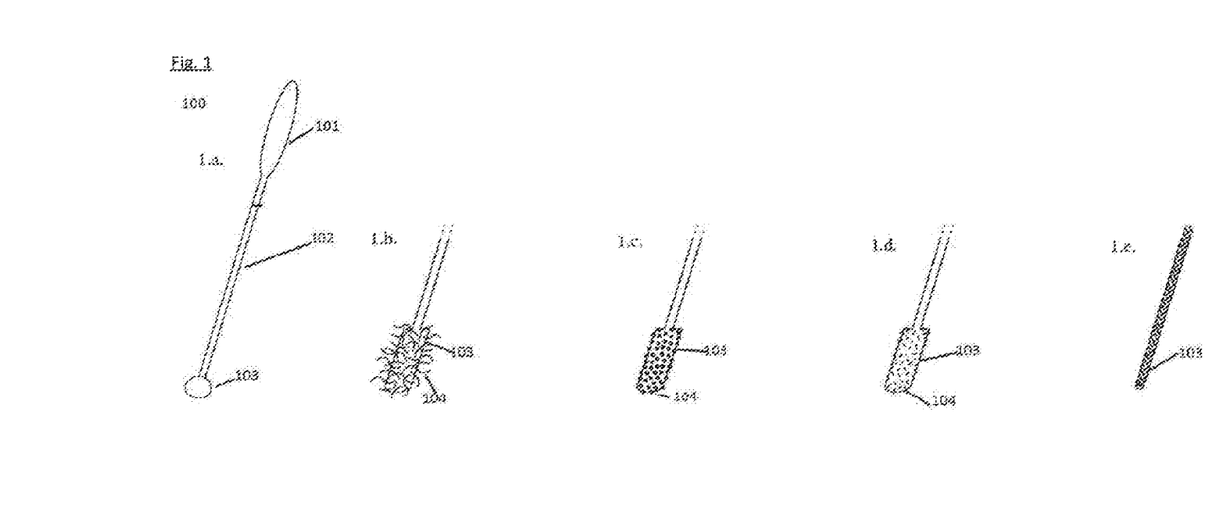

FIG. 1 represents a portable nucleic acid extraction apparatus 100. The portable nucleic acid apparatus 100 includes a handle 101, a rod 102, and a tip 103 as shown in FIG. 1.*a*. The tip of the portable nucleic acid extraction apparatus 100 may further comprise at least one structure 104 which is configured to bind nucleic acids, as represented in FIG. 1*b*. The handle 101 is proximally located on the portable nucleic acid extraction apparatus 100. A distal end 110 of the handle 101 may be in mechanical communication with a proximal end 111 of the rod 102. The handle 101 may be formed from the proximal end 111 of the rod 102, where the handle 101 and the rod 102 are formed as a single piece. The handle 101 may be a geometric shape, such as a sphere, ellipsoid, or cuboid. The handle 101 may be made of a non-reactive material, such as wood or plastic (e.g. polypropylene). The handle 101 may be made of a material that binds nucleic acids, such as polystyrene, functionalized polystyrene (e.g. functionalized with hydrofluoric acid), glass, or a silica derived material. Preferably, the handle 101 is a material that binds nucleic acids when the handle 101 and rod 102 are formed as a single piece.

The rod 102 of the portable nucleic acid extraction apparatus 100 is distal to the handle 101. The rod 102 may be a geometric shape, such as a cuboid, cylinder, or triangular prism. Preferably the rod 102 is cylindrical in shape. The rod 102 is a length that allows portability of the portable nucleic acid extraction apparatus 100, such as from 1 to 20, particularly from 2 to 15, more particularly from 3 to 10, most particularly about 5 cm in length. The rod 102 is a diameter that allows portability of the portable nucleic acid extraction apparatus 100, such as 2 to 4 millimeters. The rod 102 may be made of a non-reactive material, such as wood or plastic (e.g. or polypropylene). The rod 102 may be made of a material that binds nucleic acids, such as polystyrene, functionalized polystyrene (e.g. functionalized with hydrofluoric acid), glass, or a silica derived material.

The tip 103 is distal to the rod 102 of the portable nucleic acid extraction apparatus 100 and is configured to bind nucleic acids. The tip 103 may be in mechanical communication with the rod 102. The tip 103 may be formed from the distal end of the rod 102, thus being contiguous with the rod 102, where the tip 103 and the rod 102 are a single piece. The tip 103 may be a geometric shape, such as a sphere, cylinder, or cuboid. The tip 103 may have a similar or the same geometric shape as the rod 102. The tip 103 may be made of a non-reactive material, such as wood or plastic (e.g. polypropylene).

Alternatively, the tip 103 may be made of a material that binds nucleic acids, such as polystyrene, functionalized polystyrene (e.g. functionalized with hydrofluoric acid), glass, or a silica derived material, in particular, when the portable nucleic acid extraction apparatus 100 does not include at least one structure 104 which is configured to bind nucleic acids, such as shown in FIG. 1.e. When the portable nucleic acid extraction apparatus 100 does not comprise at least one structure 104 which is configured to bind nucleic acids, the tip 103 is made of a material which is able to bind nucleic acids. The tip 103 may comprise an increased surface area as compared to the respective perfect geometric shape, such as provided by sandblasting, for facilitation of nucleic acid binding, such as shown in FIG. 1.e.

The at least one structure 104 which is configured to bind nucleic acids may be on the tip 103 of the portable nucleic acid extraction apparatus 100. The at least one structure 104 which is configured to bind nucleic acids may be made of a nucleic acid binding medium such as polystyrene, silica, a silica derivative, silicon oxide, or an anion exchange material, which binds the nucleic acids of interest. The structure 104 may be a nucleic acid binding medium in the physical form of a fiber, a bead, or a protein. The at least one structure 104 which is a nucleic acid binding medium may further be a complementary nucleic acid sequence that is attached through derivatization to the tip 103, which is complementary to a particular nucleic acid sequence in the biological sample.

When the at least one structure 104 which is configured to bind nucleic acids is a structure in contact with the tip 103, the structure may be fibers, beads, or proteins. The structure may be contacted to the tip with an adhesive that is non-inhibitory to proteins. The structure may extend outward from the tip 103. FIG. 1.b. illustrates structures 104 configured to bind nucleic acids in the physical form of fibers, where the fibers may be silica or polystyrene. FIG. 1.c. illustrates structures 104 configured to bind nucleic acids in the physical form of beads. The beads may be silica micro beads, silica nano particles, polystyrene micro beads, polystyrene nano particles, or sand-blasted glass beads. FIG. 1.d. illustrates structures 104 configured to bind nucleic acids that are proteins. When the structure is a protein the nucleic acid may be biotinylated to increase binding to the protein. For example, when the protein is streptavidin, the nucleic acid is biotinylated for binding to the protein.

Figure 2:
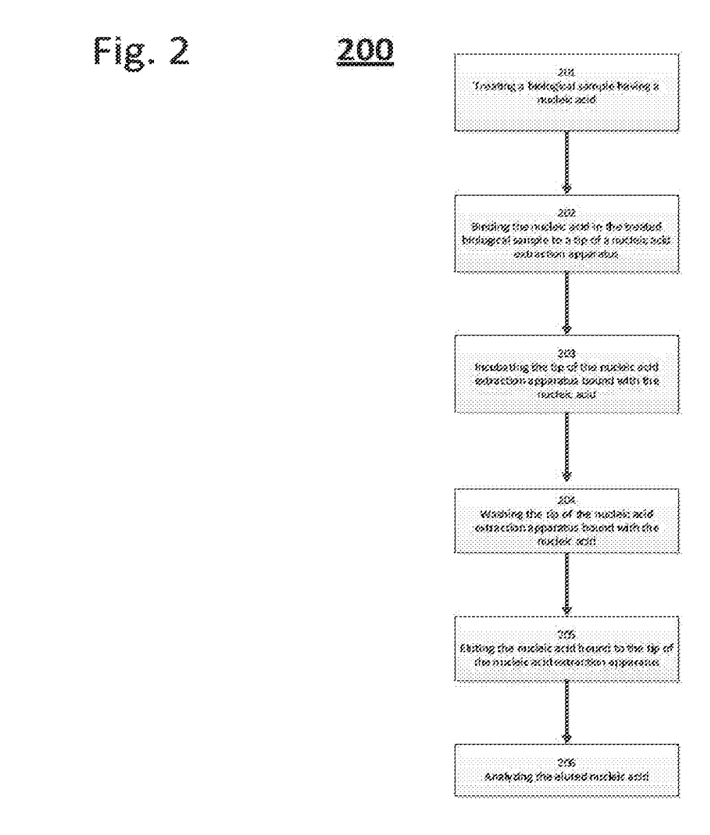
FIG. 2 illustrates a method for extracting a nucleic acid using the portable nucleic acid extraction apparatus.

FIG. 2 illustrates a method 200 for extracting nucleic acids from a biological sample. The biological sample may be blood, muscle tissue, plasma, semen, cells, cheek swabs, nasal swabs, hair follicles, buffer wash from a biological specimen, and preserved biological samples including frozen samples. In 201, the biological sample having nucleic acids is treated to extract nucleic acids. The treating includes drawing the biological sample into a first sample tube containing a lysis buffer configured for cell lysis. The first sample tube is configured to hold liquids and is made of a non-reactive material, such as glass, plastic, metal, polypropylene or ceramic. The lysis buffer is configured for lysing cells in the biological sample. For example, the lysis buffer may be 1% triton x-100 (volume triton x-100/volume water), aqueous 10 millimolar (mM) TrisHydrochloride (Tris HC1), or aqueous 1 mM ethylenediaminetetra-acetic acid (EDTA) having a pH of about 6.5, and combinations thereof. The lysis buffer may further include a lysozyme, Proteinase K, or another basic reagent (e.g. sodium hydroxide) that digests cell wall material and helps in the release of nucleic acids. The lysis buffer preferably is added in a volume approximately equal to the volume of the biological sample. The treating may further include inverting the first sample tube to mix the lysis buffer with the biological sample. When the biological sample includes durable tissue, such as muscle tissue, ear notches, tail clippings, or hair follicles, the treating may still further include incubating the first sample tube at a temperature from 37 to 95 degrees Celsius for a period of time, such as 2 minutes to 3 hours. When a basic reagent, such as sodium hydroxide, is used in the lysis buffer, the treating may further include neutralizing the buffer with an equal volume of acid, such as hydrochloric acid.

In 202, the tip of the portable nucleic acid extraction apparatus as previously described in regard to FIG. 1 binds a nucleic acid in the treated biological sample. The binding includes adding a binding buffer to the treated biological sample in the first sample tube. The binding buffer is configured to facilitate binding of nucleic acids to the tip and/or the nucleic acid binding structures of the portable nucleic acid extraction apparatus, and may be an acetate buffer, may be a citrate buffer, may comprise at least one salt, may comprise at least one chaotropic salt, may comprise biotin and reagents configured for biotinylated on nucleic acids, and any combination thereof. For example, when the tip and/or the nucleic acid binding structure of the portable nucleic acid extraction apparatus is made of glass or silica derived material, and when the biological sample is whole blood, the binding buffers may be as follows: a mixture of aqueous 6 molar (M) sodium perchlorate and aqueous 200 millimolar (mM) Glycine-hydrochloride having a pH of about 3. For further example, an acetate binding buffer may be a mixture of aqueous 50 mM Tris-hydro chloride (Tris-HC1) and aqueous sodium acetate/acetic acid having a pH of about 3.6 to 5.6; a citrate buffer may be aqueous sodium citrate/citric acid having a pH of about 3.0 to 6.2; a salt binding buffer may be aqueous 6 M sodium perchlorate, aqueous 6 M sodium nitrate, aqueous 4-5 M sodium chloride, or aqeous 4-5 M potassium chloride, aqueous sodium iodide, aqueous potassium chloride, aqueous Guanidine hydrochloride, and aqueous guanidine thiocyanate; a chaotropic salt binding buffer may be aqueous 4-6 M guanidine-hydrochloride, aqueous 4-6 M guanidine thiocyanate, aqueous 4-6 M Iodide, or aqueous 4-6 M urea, and combinations thereof. The binding buffer is added in a volume that preferably is approximately 2.5 times the volume of the biological sample.

The nucleic acid binding further includes contacting the tip of the portable nucleic acid extraction apparatus with the first sample tube, where the contacting may include moving the tip in any pattern, such as a circular motion (stirring), in the first sample tube. When the biological sample is whole blood or muscle tissue the binding may be done at room temperature (from 18 to 30 degrees Celsius).

In 203, the tip of the portable nucleic acid extraction apparatus is incubated in the biological sample to which lysis buffer and binding buffer has been added to allow for binding of nucleic acids to the tip. The incubation preferably includes adding a volume of 70 percent ethanol (volume ethanol/volume water) that is approximately 2.5 times the volume of the biological sample to the first sample tube and contacting the tip of the portable nucleic acid extraction apparatus with the first sample tube. The incubation may further include incubating the tip of the portable nucleic extraction apparatus bound with nucleic acid in the first sample tube at room temperature for at least 10 minutes.

In 204, the tip of the portable nucleic extraction apparatus with nucleic acids bound to it is washed. The washing includes contacting the tip with nucleic acids bound to it with a washing buffer in a second sample tube. The second sample tube is configured for holding liquids and is made of a non-reactive material such as glass, plastic, metal, polypropylene or ceramic. The washing buffer is configured to wash the nucleic acid to remove cellular components, except nucleic acid. The washing buffer may comprise a salt, a chaotropic salt, and combinations thereof. The washing buffer may further comprise a chelating agent, such as styrene divinylbenzene copolymer containing paired iminodiacetate ions. For example, the washing buffer may be as follows: a salt washing buffer may be aqueous 6 M sodium perchlorate, aqueous 6 M sodium nitrate, aqueous 4-5 M sodium chloride, or aqueous 4-5 M potassium chloride; a chaotropic salt washing buffer may be aqueous 4-6 M guanidine-hydrochloride, aqueous 4-6 M guanidine thiocyanate, aqueous 4-6 M Iodide, or aqueous 4-6 M urea. When the biological sample is bovine blood, and the tip and/or nucleic acid binding structure are glass or a silica derived mater, the washing buffer may include a mixture of aqueous 200 mM glycine-hydrochloride in a volume approximately equal to 2 times the volume of the biological sample, approximately 70 percent aqueous ethanol (volume ethanol/ volume of water) in a volume approximately equal to 2.5 times the volume of the biological sample, and combinations thereof. The washing may further include incubating the tip of the portable nucleic acid extraction apparatus in the second sample tube for approximately 5 to 10 minutes. The washing may further include repeating the washing.

In 205 the nucleic acid bound to the tip and/or nucleic acid binding medium of the portable nucleic acid extraction apparatus is eluted. The eluting includes contacting the tip with nucleic acids bound to it with an elution buffer in a third sample tube. The third sample tube is configured for holding liquids and is made of a non-reactive material such as glass, plastic, metal, polypropylene or ceramic. The elution buffer is configured for eluting the nucleic acid bound to the tip into the elution buffer, i.e. for facilitating the release of the bound nucleic acids from the tip into the elution buffer. The elution buffer may be a neutral solution of a neutral pH (from pH 7 to 8) (e.g. ultrapure water), aqueous 1 mM Tris-HCl of having a of pH 7.4 to 9.0, or aqueous 0.1 mM EDTA, and combinations thereof. The eluting may further include incubating the tip in the third sample tube from 37 to 95 degrees Celsius for approximately 10 minutes.

In 206, the eluted nucleic acid is analyzed. Analysis may include quantitative and qualitative analysis, such as absorption analysis, polymerase chain reaction (PCR) amplification optionally followed by gel electrophoresis, and rolling circle amplification optionally followed by gel electrophoresis.

Figure 4:
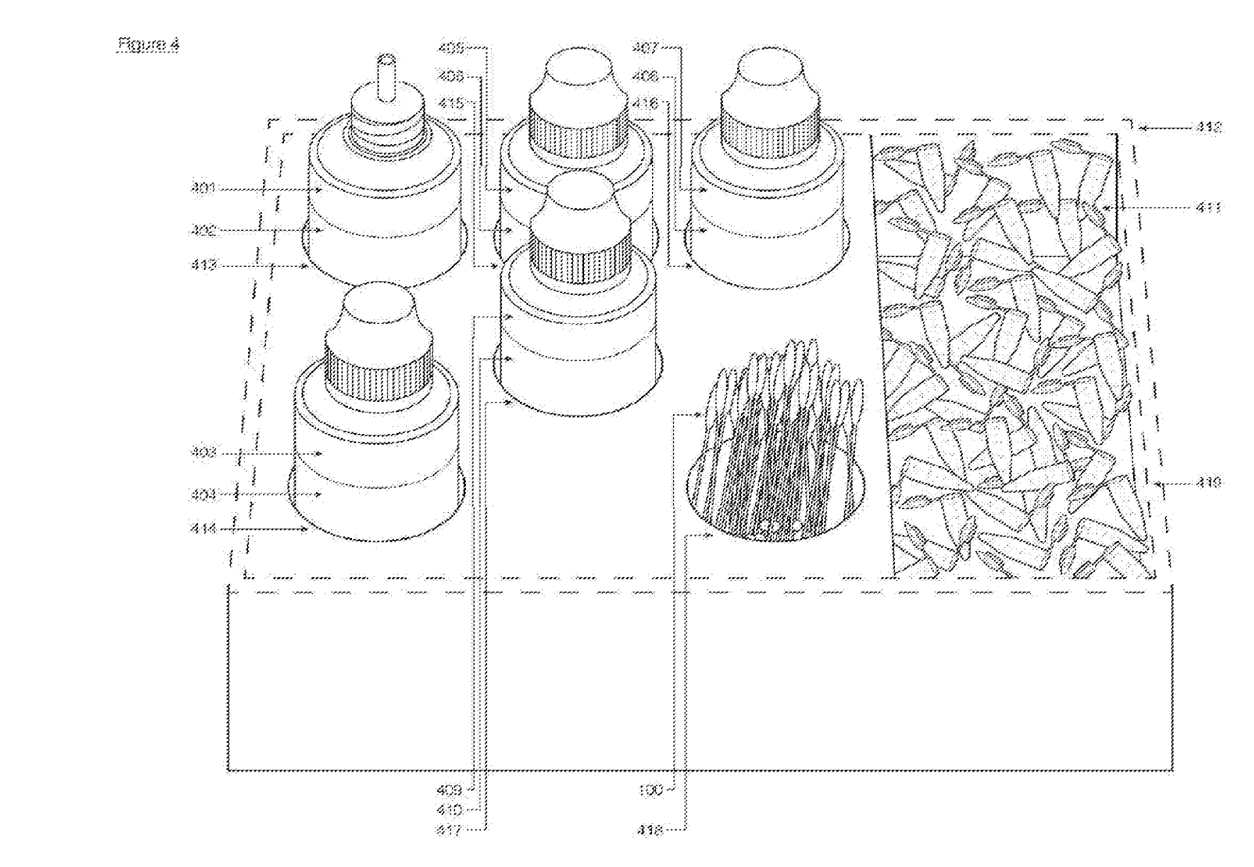
FIG. 4 depicts a portable nucleic acid extraction kit.

FIG. 4 depicts a nucleic acid extraction kit 400. The portable nucleic acid extraction apparatus may be part of a nucleic acid extraction kit 400, which may be used in the field close to the source of a biological sample (e.g. cattle, swine, poultry) or in a laboratory. The nucleic acid extraction kit 400 includes at least one nucleic acid extraction apparatus 100, at least one lysis buffer 402, at least one binding buffer 404, at least one washing buffer 406, at least one elution buffer 408, and, optionally ethanol 410, and at least three kit sample tubes 411. The buffers are typically provided in separate bottles 401, 403, 405, 407 and, optionally, ethanol is provided in a fifth bottle 409. The portable nucleic acid extraction kit optionally further comprises a container 412. Preferably the nucleic acid extraction kit 400 includes at least 50 portable nucleic acid extraction apparatuses, at least 150 kit sample tubes, the first bottle having a volume of lysis buffer to treat at least 50 biological samples, the second bottle having a volume of binding buffer to bind nucleic acids of at least 50 biological samples, a third bottle having a volume of washing buffer to wash at least 50 biological samples, and a fourth bottle having a volume of elution buffer to elute nucleic acids of at least 50 biological samples.

The portable nucleic acid extraction apparatus 100 in the nucleic acid extraction kit 400 may be wrapped in a material (not pictured) to prevent atmospheric contaminants from contacting the portable nucleic acid extraction apparatus, such as a polymeric wrap, paper, or aluminum foil.

The first bottle 401 is made of a non-reactive material, such as glass, plastic, metal, polypropylene or ceramic. The first bottle 401 is configured to hold liquids when inverted, such as by a cap, rubber stopper, screw cap, or dropper tube. The first bottle 401 may be flexible and configured to deliver the lysis buffer 401, such as, through a Yorker tip by squeezing the first bottle.

The second bottle 403 is made of a non-reactive material, such as glass, plastic, metal, polypropylene or ceramic. The second bottle 403 is configured to hold liquids when inverted, such as by a cap, rubber stopper, screw cap, or dropper tube. The second bottle 403 may be flexible and configured to deliver the binding buffer 403, such as, through the Yorker tip by squeezing the second bottle.

The third bottle 405 is made of a non-reactive material, such as glass, plastic, metal, polypropylene or ceramic. The third bottle 405 is configured to hold liquids when inverted, such as by a cap, rubber stopper, screw cap, or dropper tube. The third bottle 405 may be flexible and configured to deliver the washing buffer through the Yorker tip, such as by squeezing the third bottle.

The fourth bottle 407 is made of a non-reactive material, such as glass, plastic, metal, polypropylene or ceramic. The fourth bottle 407 is configured to hold liquids when inverted, such as by a cap, rubber stopper, screw cap, or dropper tube. The fourth bottle 407 may be flexible and configured to deliver the lysis buffer through the Yorker tip, such as by squeezing the fourth bottle.

The fifth bottle 409 is made of a non-reactive material, such as glass, plastic, metal, polypropylene or ceramic. The fifth bottle 409 is configured to hold liquids when inverted, such as by a cap, rubber stopper, screw cap, or dropper tube. The fifth bottle 409 may be flexible and configured to deliver the ethanol, such as, through the Yorker tip by squeezing the fifth bottle.

The sample kit tubes 411 are configured to hold liquids and are made of a non-reactive material, such as glass, plastic, metal, polypropylene or ceramic. The sample kit tubes may further be configured to hold liquids when inverted, such as through a cap, lid, or rubber stopper.

The container 412 is configured to contain at least one nucleic acid extraction apparatus 100, a first bottle 401 containing a lysis buffer 402, a second bottle 403 containing a binding buffer 404, a third bottle 405 containing a washing buffer 406, a fourth bottle 407 containing an elution buffer 408, optionally a fifth bottle 409 containing ethanol 410, and at least three kit sample tubes 411 (contents of the kit). The container may be of any non-reactive material, such as cardboard, plastic, or polystyrene. The container may be of any geometric shape configured for the holding the contents of the kit, such as a cuboid, cylinder, or triangular prism.

The container may further include a first compartment 413 configured to hold the first bottle 401, a second compartment 414 configured to hold the second bottle 403, a third compartment 415 configured to hold the third bottle 405, a fourth compartment 416 configured to hold the fourth bottle 407, optionally a fifth compartment 417 configured to hold the fifth bottle 409, a sixth compartment 418 configured to hold the at least one nucleic acid extraction apparatus 100, and a seventh container 419 configured to hold the at least three kit sample tubes 411. The first compartment 413, second compartment 414, third compartment 415, fourth compartment 416, fifth compartment 417, sixth compartment 418, and seventh compartment 419 may be formed by any non-reactive material such as cardboard, plastic, or polystyrene. The container may further include a closure (not pictured) to keep the contents of the kit in the container when inverted. The closure may be of any non-reactive material, such as cardboard, plastic, or polystyrene.

The present invention further relates to the following embodiments.

In particular embodiments, the present invention relates to a portable nucleic acid extraction kit comprising: a container, the container including, a portable nucleic acid extraction apparatus comprising, a handle, a rod attached to the handle, and a tip attached to the rod, where the tip is a material selected from at least one of the group consisting of wood, plastic, polystyrene, functionalized polystyrene, glass, and a silica-derived material; a lysis buffer in a first bottle; a binding buffer in a second bottle; a washing buffer in a third bottle; an elution buffer in a fourth bottle; and at least three kit sample tubes.

In particular embodiments, the container further includes a volume ethanol in a fifth bottle.

In particular embodiments, the portable nucleic acid extraction apparatus further comprises a nucleic acid binding medium, where the nucleic acid binding medium is configured to bind nucleic acids.

In particular embodiments, the present invention relates to a portable nucleic acid extraction apparatus for nucleic acid extraction, comprising: a handle; a rod attached to the handle; and a tip attached to the rod, where the tip is a material selected from at least one of the group consisting of wood, plastic, polystyrene, functionalized polystyrene, glass, and a silica-derived material.

In particular embodiments, the portable nucleic acid extraction apparatus further comprises a nucleic acid binding medium attached to the tip, where the nucleic acid binding medium is configured to bind nucleic acids.

In particular embodiments, the handle, the rod, and the tip are formed as a single piece, where the material that forms the handle, the rod, and the tip is selected from at least one of the group consisting of wood, plastic, polystyrene, functionalized polystyrene, glass, and a silica-derived material.

In particular embodiments, the handle, the rod, and the tip are glass.

In particular embodiments, the handle, the rod, and the tip are glass sandblasted to increased surface area.

In particular embodiments, the tip is configured to bind nucleic acids and is selected from at least one of the group consisting of polystyrene, functionalized polystyrene, glass, and silica-derived material.

In particular embodiments, the tip is glass sandblasted to increased surface area.

In particular embodiments, the nucleic acid binding medium is in the form of a fiber.

In particular embodiments, the fiber is a silica fiber.

In particular embodiments, the fiber is a polystyrene fiber.

In particular embodiments, the nucleic acid binding medium is in the form of a bead.

In particular embodiments, the bead is selected from the group consisting of silica micro beads, silica nano particles, polystyrene micro beads, polystyrene nano particles, sandblasted glass beads, and combinations thereof.

In particular embodiments, the nucleic acid binding medium is a protein.

In particular embodiments, the present invention relates to a nucleic acid analysis method for analyzing nucleic acids using a portable nucleic acid extraction apparatus, comprising: treating a biological sample having a nucleic acid with a lysis buffer to lyse cells in the biological sample; binding the nucleic acid in the treated biological sample to a tip of a portable nucleic acid extraction apparatus with a binding buffer; incubating the tip of the portable nucleic acid extraction apparatus bound with the nucleic acid; washing the tip of the portable nucleic acid extraction apparatus bound with the nucleic acid with a washing buffer; eluting the nucleic acid bound to the tip of the portable nucleic acid extraction apparatus with an elution buffer; and analyzing the eluted nucleic acid.

In particular embodiments, the incubating further includes contacting the tip of the portable nucleic acid extraction apparatus with a volume of ethanol.

In particular embodiments, the lysis buffer is an aqueous solution of 10 millimolar tris-hydrochloride; the binding buffer is a combination of aqueous 6 molar sodium hypochlorite and aqueous 200 millimolar glycine-hydrochloride having a pH from 2.0 to 4.0; the washing buffer is a combination of aqueous glycine-hydrochloride and aqueous ethanol (volume ethanol/volume of water); and the elution buffer is aqueous tris-hydrochloride having a pH from 7.0 to 10.0.

In particular embodiments, the lysis buffer further comprises a substance chosen from the group consisting of lysozyme, proteinase k, and sodium hydroxide.

In particular embodiments, the lysis buffer is selected from the group consisting from 0.2 to 5 percent triton x-100 (volume triton x-100/volume water), from 2 to 50 millimolar aqueous tris-hydrochloride, and aqueous 1 millimolar ethylenediaminetetra-acetic acid having a pH from 5.5 to 7.5, and combinations thereof; the binding buffer is selected from the group consisting of a mixture of aqueous sodium hypochlorite and glycine-hydrochloride having a pH from 2.0 to 4.0, a mixture of aqueous tris-hydrochloride and aqueous sodium acetate/acetic acid having a pH from 3.6 to 5.6; aqueous sodium citrate/citric acid having a pH from 3.0 to 6.2, aqueous 5 to 7 molar sodium perchlorate, aqueous 6 molar sodium nitrate, aqueous 4 to 5 molar sodium chloride, aqueous 4 to 5 molar potassium chloride, aqueous 4 to 6 molar guanidine-hydrochloride, aqueous 4 to 6 molar guanidine thiocyanate, aqueous 4 to 6 molar iodide, and aqueous 4 to 6 molar urea, and combinations thereof the washing buffer is selected from the group consisting of aqueous 5 to 7 molar sodium perchlorate, aqueous 5 to 7 molar sodium nitrate, aqueous 4 to 5 molar sodium chloride, aqueous 4 to 5 molar potassium chloride, aqueous 4 to 6 molar guanidine-hydrochloride, aqueous 4 to 6 molar guanidine thiocyanate, aqueous 4 to 6 M iodide, aqueous 4 to 6 molar urea, and aqueous 100 to 300 millimolar glycine-hydrochloride, and combinations thereof; the elution buffer is selected from the group consisting of ultrapure water, aqueous tris-hydrochloride having a pH from 7.4 to 9, and from 0.05 to 0.2 millimolar aqueous ethylenediaminetetra-acetic acid, and combinations thereof.

The following examples are provided to illustrate one or more preferred embodiments of the invention. Numerous variations can be made to the following examples that lie within the scope of the invention.

EXAMPLE 1

Figure 3:
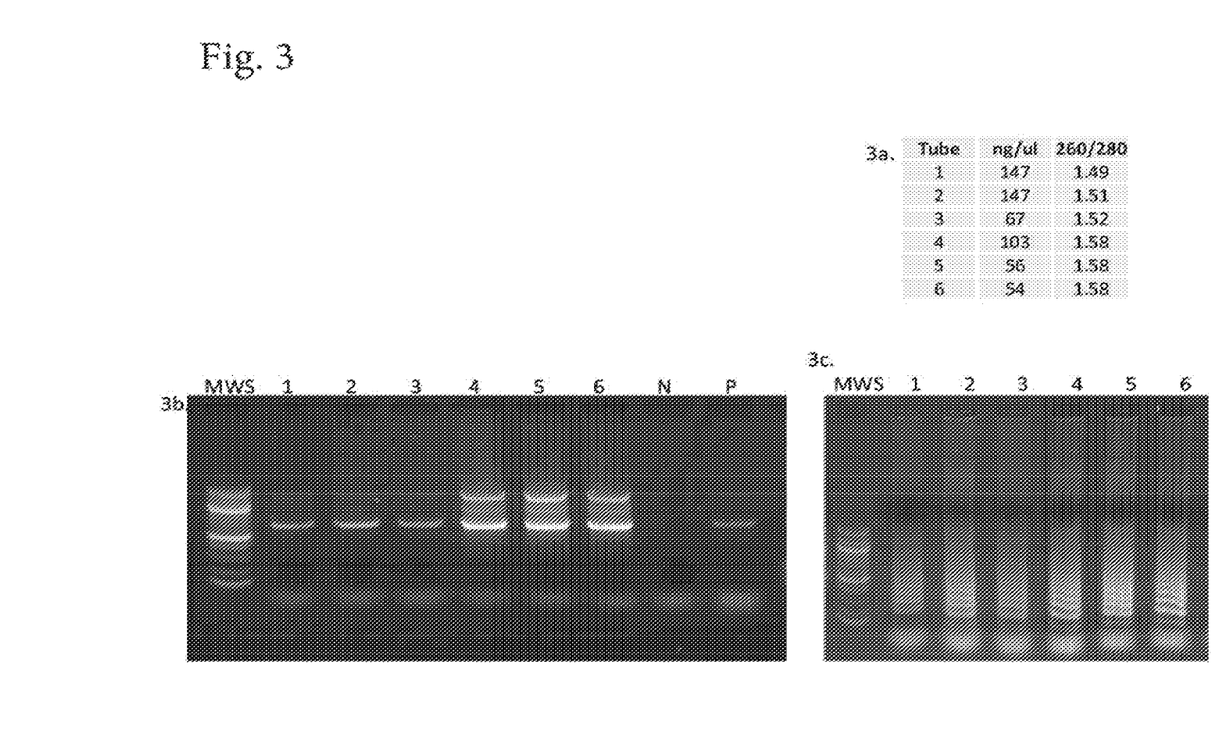

Determining concentration of extracted genomic DNA. FIG. 3.a. illustrates a concentration and purity determination of extracted genomic DNA. Genomic DNA from a biological sample was extracted using the method 200. The biological sample was six 100 microliter aliquots of bovine blood. The lysis 201 was performed with 0.01 mM Tris-HCl at pH 6.8 as lysis buffer. While a specific lysis buffer was used in this instance other lysis buffers may be used. The binding 202 included the addition of 6M Sodium hypochlorite in 200 mM glycine-hydrochloride at pH 3.0 as binding buffer. While a specific binding buffer was used in this instance other binding buffers may be used. The incubation 203 included adding ethanol and stirring the treated biological sample for 10 minutes. The washing 204 was performed with 200 microliters of 200 mM glycine-hydrochloride and 250 uL of 70% (volume/volume) ethanol as washing buffer and included stirring the treated biological sample for between 2 to 5 minutes. While a specific washing buffer was used in this instance other washing buffers may be used. The elution 205 was performed with 10 mM Tris-HCl buffer at pH 8.8 as elution buffer and included incubation for 10 minutes at 90 degrees Celsius. While a specific elution buffer was used in this instance other elution buffers may be used. The analysis 206 included the measurement of DNA concentration and purity. DNA concentration was measured by DNA absorbance of ultra violet visible light by a spectrophotometer and purity was measured by calculating the ration of absorbance reading at 260 nanometers (nm) and 280 nm. FIG. 3.a. demonstrates that the portable nucleic acid extraction apparatus and method 200 of extraction yields DNA of a quality that is accepted as good (e.g. having an absorbance ration from 1.3 to 1.8) and suitable for further application and quantitative analysis.

EXAMPLE 2

PCR amplification and gel electrophoresis. FIG. 3.b. illustrates PCR amplification and gel electrophoresis of the bovine glyceraldehyde 3-phosphate dehydrogenase (GAPDH) gene, using genomic DNA extracted with method 200 as a template. Six 100 microliter aliquots of bovine blood were used as starting material. The method 200 of Example 1 was used to extract the genomic DNA of these biological samples. The analysis 206 included PCR amplification of the GAPDH gene using 1 microliter eluate obtained from each of the 6 samples in 15 microliter PCR reactions. The 6 PCR reaction products were run on a 1% agarose gel and stained with SYBR green to visualize the extracted DNA. Lanes 1 through 6 correspond to each of the 6 PCR products obtained. Lane N is a negative control. Lane P is a positive control, which used 40 nanograms bovine genomic DNA as template for PCR amplification of the GAPDH gene. FIG. 3.b. illustrates a distinct PCR product of about 650 base pairs in each of lanes 1 through 6 indicating that the portable nucleic acid extraction apparatus and method 200 yield extracted genomic DNA which is suitable for subsequent PCR amplification, e.g., to qualitatively determine the presence or absence of a given DNA sequence.

EXAMPLE 3

Rolling Circle Amplification (RCA) and gel electrophoresis. FIG. 3.c. illustrates RCA and gel electrophoresis for a region of the bovine beta casein gene, using genomic DNA extracted with the method 200 as template. Six 100 microliter aliquots of bovine blood were used as starting material. The method 200 of Example 1 was used to extract genomic DNA from these biological samples. The analysis 206 included ligation of specific padlock probes to the bone beta casein gene in the extracted genomic DNA from the biological sample and amplification of the ligated padlock probe specific primers using Bst DNA polymerase. The six amplification products were run on a 1% agarose gel and stained with SYBR green to visualize the amplified DNA. The lane marked MWS is a size standard control lane included a 100 base pair molecular weight ladder. FIG. 3.c. illustrates a visualization of banding patterns in lanes 1 through 6 that is indicative of the amplification of the padlock probe specific to the bovine beta casein gene, which indicates that the portable nucleic acid extraction apparatus and method 200 yield extracted genomic DNA that is suitable for subsequent Rolling Circle Amplification, e.g., to qualitatively determine the presence or absence of a given DNA sequence.

The invention claimed is:

1. A portable nucleic acid extraction apparatus for nucleic acid extraction, comprising:
   a handle having a distal end, where the handle is cylindrical in shape;
   a rod having a proximal end, where the rod is cylindrical in shape having a diameter from 2-4 millimeters and a length of 1 to 20 centimeters, wherein the proximal end of the rod is attached to the distal end of the handle; and
   a tip attached to the rod, where an end of the tip opposite to the rod is closed where an interior of the tip cannot contact nucleic acids, where the tip comprises a material chosen from at least one of polystyrene, functionalized polystyrene, and a silica-derived material,
   wherein the portable nucleic acid extraction apparatus does not comprise specialized equipment selected from the group consisting of pipettes, centrifuges, and automated equipment; and
   wherein the portable nucleic acid extraction apparatus does not comprise a nucleic acid binding medium that is stationary and not attached to the portable nucleic acid extraction apparatus.

2. The portable nucleic acid extraction apparatus of claim 1, wherein
   the handle, the rod, and the tip are formed as a single piece, where the tip has a cylindrical shape, where the material that forms the handle, the rod, and the tip is selected from at least one of the group consisting of polystyrene, functionalized polystyrene, and a silica-derived material.

3. The portable nucleic acid extraction apparatus of claim 2, wherein
the handle, the rod, and the tip are silica-derived material, and wherein the tip is sandblasted.

4. The portable nucleic acid extraction apparatus of claim 2, wherein
the handle, the rod, and the tip are glass sandblasted to increased surface area.

5. The portable nucleic acid extraction apparatus of claim 1, wherein
the tip is spherical in shape and is configured to bind nucleic acids.

6. The portable nucleic acid extraction apparatus of claim 1, wherein
the tip is glass sandblasted to increased surface area.

7. A portable nucleic acid extraction apparatus for nucleic acid extraction, comprising:
a handle having a distal end;
a means for allowing portability of the portable nucleic acid extraction apparatus between a first sample tube and a second sample tube, and between a second sample tube and a third sample tube, the means attached to the distal end of the handle; and
a tip attached to the means, where an end of the tip opposite to the means is closed where an interior of the tip cannot contact nucleic acids, where the tip comprises a material chosen from at least one of polystyrene, functionalized polystyrene, and a silica-derived material, wherein the portable nucleic acid extraction apparatus does not comprise specialized equipment selected from the group consisting of pipettes, centrifuges, and automated equipment; and
wherein the portable nucleic acid extraction apparatus does not comprise a nucleic acid binding medium that is stationary and not attached to the portable nucleic acid extraction apparatus.

8. The nucleic acid extraction apparatus of claim 1, wherein the material of the tip is configured to bind nucleic acids in an acidic buffer having a pH below 6.0.

9. The nucleic acid extraction apparatus of claim 1, wherein the material of the tip is configured to bind nucleic acids in an acidic buffer having a pH below 6.0 and at least one salt.

10. The nucleic acid extraction apparatus of claim 7, wherein The material of the tip is configured to bind nucleic acids in an acidic buffer having a pH below 6.0.

11. the nucleic acid extraction apparatus of claim 7, wherein The material of the tip is configured to bind nucleic acids in an acidic buffer having a pH below 6.0 and at least one salt.

* * * * *